(12) United States Patent
Van De Venne et al.

(10) Patent No.: US 6,469,009 B1
(45) Date of Patent: Oct. 22, 2002

(54) PHARMACEUTICAL COMPOSITIONS FOR THE TREATMENT OF RHINITIS

(75) Inventors: Herman Van De Venne, Lasne (BE); Jean-Pierre Martin, Montigny-le-Tilleul (BE)

(73) Assignee: UCB, S.A., Brussels (BE)

( * ) Notice: Subject to any disclaimer, the term of this patent is extended or adjusted under 35 U.S.C. 154(b) by 1191 days.

(21) Appl. No.: 08/629,144

(22) Filed: Apr. 8, 1996

(51) Int. Cl.$^7$ .................... A61K 31/495; A61K 31/135
(52) U.S. Cl. ........................ 514/255; 514/653
(58) Field of Search ................. 514/255, 653

(56) References Cited

U.S. PATENT DOCUMENTS

| | | | | |
|---|---|---|---|---|
| 4,525,358 A | * | 6/1985 | Baltes et al. ................. | 514/255 |
| 4,800,162 A | | 1/1989 | Matson ........................ | 435/280 |
| 4,990,535 A | * | 2/1991 | Cho et al. ................... | 514/556 |
| 5,057,427 A | | 10/1991 | Wald et al. ................. | 435/280 |

FOREIGN PATENT DOCUMENTS

| | | |
|---|---|---|
| GB | 2 225 321 | 5/1990 |
| WO | WO88/09656 | 12/1988 |
| WO | WO92/04022 | 3/1992 |
| WO | WO94/06429 | 3/1994 |
| WO | WO94/06430 | 3/1994 |
| WO | WO94/08551 | 4/1994 |
| WO | WO94/25009 | 11/1994 |
| WO | WO95/07103 | 3/1995 |

OTHER PUBLICATIONS

Handbook of Nonprescription Drugs, 18th ed. published by the American Pharmaceutical Association, pp 127–152 and 165–171, 1986.*

Grosclaude et al., Allergy–European Journal of Allergy and Clinical Immunology, Abstracts XVI, European Congress of Allergology and Clinical Immunology, Madrid, Spain Jun. 25–30, 1995, No. 2—vol. 50 Abstract P–0066.

* cited by examiner

*Primary Examiner*—Raymond Henley, III
(74) *Attorney, Agent, or Firm*—Wenderoth, Lind & Ponack, L.L.P.

(57) ABSTRACT

A pharmaceutical composition comprising a therapeutically effective amount of a mixture consisting essentially of (i) pseudoephedrine, an individual optical isomer or a pharmaceutically acceptable salt thereof, and
(ii) at least one compound selected from 2-[4-(diphenylmethyl)-1-piperazinyl]-acetic acid or amide derivatives, an individual optical isomer or a pharmaceutically acceptable salt thereof.

14 Claims, No Drawings

PHARMACEUTICAL COMPOSITIONS FOR THE TREATMENT OF RHINITIS

The present invention is in the area of pharmaceutical compositions and methods of treatment of diseases in humans. More particularly the invention relates to combinations of two or more than two pharmaceutical substances and methods of treatment of allergic disorders.

BACKGROUND OF THE INVENTION

U.S. Pat. No. 4,525,358 discloses 2-[4-(diphenylmethyl)-1-piperazinyl]-acetic acids or amides thereof having the formula

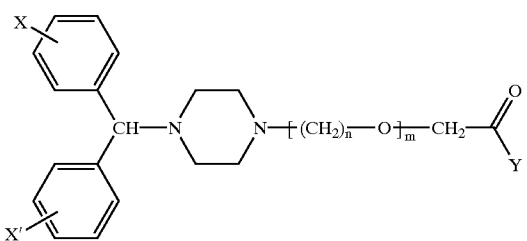

wherein

Y is a hydroxyl group or an —NH$_2$ group,

X and X' represent independently a hydrogen atom, a halogen atom, a straight or branched chain lower alkoxy radical or a trifluoromethyl radical, m is 1 or 2, and n is 1 or 2, or a non-toxic, pharmaceutically acceptable salt thereof.

The compounds of formula I possess interesting pharmacological properties. In particular, they are useful as antiallergic, antihistaminic, bronchodilatory and antispasmodic agents.

Several patent documents already disclosed binary and/or ternary combinations of pharmaceutical substances in specific amounts in view of treating various disorders in humans. In particular International Patent Application published as WO 88/09656 discloses pharmaceutical compositions of matter comprising an analgesically effective amount of aspirin, sodium salicylate, salicylamide or acetaminophen, in combination with a non-sedating antihistamine, one or more active components selected from a decongestant, cough suppressant, expectorant and further optionally including pharmaceutically acceptable carriers therefor.

International Patent Application published as No. WO 92/04022 discloses compositions for the treatment of cold, cold-like flu and flu-like symptoms comprising an effective amount of a naphthalene derivative and optionally containing one or more therapeutic agents such as decongestant, an antitussive, an expectorant, an antihistamine or a bronchodilatator. Similar examples of combinations of pharmaceutically active substances may be found also in International Patent Publications No. WO 94/08551, No. WO 94/25009 and No. WO 95/07103.

Some documents also disclose the use of specific stereoisomers of pharmaceutical substances for treating disorders in humans while avoiding adverse effects associated with the corresponding racemic mixture. In particular International Patent Applications published as WO 94/06429 and WO 94/06430 disclose methods of treating a condition caused by or contributed to by eosinophilia or enhanced eosinophil function in a human, which comprises administering to a human, in need of eosinophilic therapy, an amount of (+) cetirizine (respectively (−) cetirizine), or a pharmaceutically acceptable salt thereof, substantially free of its (−) stereoisomer (respectively its (+) stereoisomer), said amount being sufficient to alleviate said eosinophilia or enhanced eosinophil function but insufficient to cause said adverse effects.

On the other hand, pseudoephedrine, its hydrochloride and sulfate are well known sympathomimetic drugs recognised as safe therapeutic agents effective in the relief of nasal congestion.

It is well known to those skilled in the art that combinations of pharmaceutical substances should always be handled with care because they are very susceptible of inducing impredictable adverse effects in humans. In some cases, they also induce an efficiency of the treatment which is lower than that of each pharmaceutical substance taken alone.

In the treatment of allergic disorders such as for example a pollen associated allergic rhino-conjunctivitis, care should be taken, when combining an antihistaminic and a decongestant, not only to increase the overall efficiency of the treatment, i.e. the percentage of days during the whole treatment period, when the symptoms of sneezing, rhinorrhea, nasal obstruction, lacrimation, nasal and ocular pruritus are absent or at the most mild, but also to avoid possible adverse effects like insomnia and headache.

Thus an objective of the present invention is to provide a useful combination of pharmaceutical substances for treating various disorders in humans, said combination being able to increase the efficiency of said treatment over the efficiency of each substance alone, while avoiding adverse effects during the said treatment.

Another objective of the present invention is to provide such a useful combination of pharmaceutical substances when the treatment in question is a therapy such as needed for rhinitis, cold, flu, cold-like and flu-like symptoms.

SUMMARY OF THE INVENTION

The present invention is based on the unexpected recognition that the combined use of pseudoephedrine, an individual optical isomer or a pharmaceutically acceptable salt thereof on the one hand and a 2-[4-(diphenylmethyl)-1-piperazinyl]-acetic acid or amide derivative, an individual optical isomer or a pharmaceutically acceptable salt thereof on the other hand in the treatment of rhinitis, cold, flu, cold-like and flu-like symptoms results in improved efficiency over each pharmaceutical substance alone based on the patients daily evaluation of symptoms like sneezing, rhinorrhea, nasal obstruction, nasal and ocular pruritus and lacrymation. This improved primary efficiency was obtained without increasing possible adverse effects of the treatment, like insomnia and headache.

DETAILED DESCRIPTION OF THE INVENTION

The present invention encompasses a method of treating a disorder selected from rhinitis, cold, flu, cold-like and flu-like symptoms in a human, which comprises administering to a human in need of such therapy, simultaneously or separately, an effective amount of (i)pseudoephedrine, an individual optical isomer or a pharmaceutically acceptable salt thereof and an effective amount of (ii) at least one compound selected from 2-[4-(diphenylmethyl)-1-piperazinyl]-acetic acid or amide derivatives, an individual optical isomer or a pharmaceutically acceptable salt thereof.

When administration is effected simultaneously, it is preferably in the form of a pharmaceutical composition comprising a therapeutically effective amount of a mixture consisting essentially of compounds (i) and (ii). Such administration in a single dosage form is preferred.

The term separately as used herein means that compounds (i) and (ii) are administered separately but within a close time proximity, i.e. a lapse of time which is sufficiently short, e.g. not higher than about 3 hours, to keep advantage of their combined therapeutic effects.

The term "a method for treating a disorder selected from rhinitis, cold, flu, cold-like and flu-like symptoms in a human" as used herein means providing relief from the symptoms of sneezing, rhinorrhea, nasal obstruction, nasal and ocular pruritus, lacrymation, and the like.

The term "2-[4-(diphenylmethyl)-1-piperazinyl]-acetic acid or amide derivative" as used herein means a compound having the formula

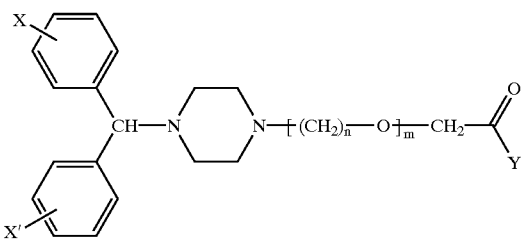

(I)

wherein

Y is a hydroxyl group or an —NH$_2$ group,

X and X' represent independently a hydrogen atom, a halogen atom, a straight or branched chain lower alkoxy radical or a trifluoromethyl radical, m is 1 or 2, and n is 1 or 2.

The term "lower alkoxy" as used herein means residues of both straight and branched chain aliphatic alcohols having from 1 to 4 carbon atoms, such as methoxy, ethoxy, propoxy and the like. The halogen atom is preferably a chlorine or fluorine atom.

The term "pharmaceutically acceptable salts" as used herein with respect to 2-[4-(diphenylmethyl)-1-piperazinyl]-acetic acid or amide derivatives means not only their addition salts with non-toxic organic and inorganic acids, such as acetic, citric, succinic, ascorbic, hydrochloric, hydrobromic, sulfuric, and phosphoric acids and the like, but also their metal salts (for example sodium or potassium salts), ammonium salts, amine salts and aminoacid salts.

The term "pharmaceutically acceptable salt" as used herein with respect to pseudoephedrine means namely its hydrochloride and sulfate and equivalent non-toxic salts.

The term "individual optical isomer" as used herein means, when the molecule has a centre of asymmetry, the levorotatory and the dextrorotatary enantiomers thereof. As is well known in the art, purification of such enantiomers is a rather difficult process depending upon the selected way of preparation of the compound and the optical purity of the starting material. Therefore the term "individual optical isomer" as used herein means that the said compound comprises at least 90%, preferably at least 95%, by weight of the said individual (either dextro- or levorotatory) optical isomer and at most 10%, preferably at most 5%, by weight of the other individual (respectively levo- or dextrorotatary) optical isomer. Each individual optical isomer may be obtained from its racemic mixture by using conventional means such as disclosed in British patent application No. 2,225,321. Additionally, each individual optical isomer can be prepared from the racemic mixture by enzymatic biocatalytic resolution, such as disclosed in U.S. Pat. Nos. 4,800,162 and 5,057,427.

Preferred compounds (ii) used in the compositions of the invention include:

2-[2-[4-[(4-chlorophenyl)phenylmethyl]-1-piperazinyl] ethoxy]-acetic acid, as a racemate, a levorotatory or dextrorotatory enantiomer, and their pharmaceutically acceptable salts, namely their dihydrochloride and potassium salts;

2-[2-[4-(diphenylmethyl)-1-piperazinyl]ethoxy]-acetic acid or its dihydrochloride;

2-[2-[4-[(4-fluorophenyl)phenylmethyl]-1-piperazinyl] ethoxy]-acetic acid or its hydrate;

2-[2-[4-[bis(4-fluorophenyl)methyl]-1-piperazinyl]ethoxy]-acetic acid;

2-[2-[4-(diphenylmethyl)-1-piperazinyl]ethoxy]-acetamide or its dihydrochloride;

2-[2-[4-[(2-chlorophenyl)phenylmethyl]-1-piperazinyl] ethoxy]-acetamide or its dihydrochloride;

2-[2-[2-[4-[(4-methoxyphenyl)phenylmethyl]-1-piperazinyl]ethoxy]ethoxy]-acetamide or its dihydrochloride;

2-[2-[2-[4-(diphenylmethyl)-1-piperazinyl]ethoxy] ethoxy]acetamide or its dihydrochloride;

2-[2-[2-[4-[(4-chlorophenyl)phenylmethyl]-1-piperazinyl] ethoxy]ethoxy]-acetamide or its dihydrochloride;

2-[2-[2-[4-(diphenylmethyl)-1-piperazinyl]ethoxy]ethoxy]-acetic acid or its dihydrochloride;

2-[2-[2-[4-[(4-chlorophenyl)phenylmethyl]-1-piperazinyl] ethoxy]ethoxy]-acetic acid or its dihydrochloride;

The most preferred compounds (ii) are the racemate of 2-[2-[4-[(4-chlorophenyl)phenylmethyl]-1-piperazinyl] ethoxy]-acetic acid and its dihydrochloride salt which is well known as cetirizine dihydrochloride, and its levorotatory and dextrorotatory enantiomers.

For implementing the method of treatment of the invention the composition hereinabove described should contain an effective amount of the mixture of the compounds (i) and (ii). An effective amount can be readily determined by the use of conventional techniques and by observing results obtained under analogous circumstance. In determining the effective amount, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective amount of the mixture of the compounds (i) and (ii) in the composition of the invention will generally vary from about 0.1 milligram per kilogram of body weight per day (mg/kg/day) to about 6 mg/kg/day. A posology (dose) of about 15 mg to about 300 mg once or twice per day is preferred.

Additionally, the respective proportions of compound (i) and compound (ii) in the mixture should preferably be such that the said composition consists essentially of about 1 to about 30 percent by weight, more preferably about 3 to about 15 percent by weight of the compound (ii) and of about 70 to about 99 percent by weight, more preferably about 85 to about 97 percent by weight of the compound (i).

A composition according to the invention can be administered to a patient in any form or mode which makes the composition bioavailable in effective amounts, namely the oral route. For example, it can be administered orally, intranasally, or rectally. Oral administration is generally preferred. One skilled in the art of preparing formulations can readily select the proper form and mode of administration depending upon the particular characteristics of the disease state to be treated, the stage of the disease, and other relevant circumstances.

The compositions of the invention can comprise the mixture of compounds (i) and (ii) alone or such mixture in combination with at least one pharmaceutically acceptable carrier or excipient, the proportion and nature of which are determined by the solubility and chemical properties of the composition selected, the chosen route of administration, and standard pharmaceutical practice.

More particularly, the present invention contemplates pharmaceutical compositions consisting essentially of a therapeutically effective amount of the above-described mixture of compounds (i) and (ii) in admixture or otherwise in association with one or more pharmaceutically acceptable carriers or excipients (collectively referred to hereafter as "carrier" materials).

The carrier material may be a solid, semi-solid, or liquid material which can serve as a vehicle or medium for the active ingredient. Suitable carrier materials are well known in the art. The pharmaceutical compositions of the invention may be adapted for oral use and may be administered to the patient in the form of tablets, capsules, powders, elixirs, syrups, solutions, suspensions, or the like. The pharmaceutical composition of the invention may also be adapted for rectal use and may then be administered to the patient in the form of suppositories.

The carrier material should be suitably selected with respect to the intended form of administration, and consistent with conventional pharmaceutical practice. For instance, for oral administration in the form of tablets or capsules, the therapeutically active drug components may be combined with any oral non-toxic pharmaceutically acceptable inert carrier such as lactose or starch. Optionally, the pharmaceutical composition of the invention also contain a binder such as microcrystalline cellulose, gum tragacanth or gelatine, a disintegrating agent such as alginic acid, a lubricant such as magnesium stearate, a glidant such as colloidal silicon dioxide, a sweetening agent such as sucrose or saccharin, a coloring agent or a flavouring agent such as peppermint or methyl salicylate Because of their easy administration, tablets and capsules represent the most advantageous oral dosage unit form. If desired, tablets may be coated by standard aqueous or nonaqueous techniques with sugar, shellac or other entering coating agents. Desirably, each tablet or capsule contains from about 15 mg to about 300 mg of the mixture of active ingredients.

In addition to the common dosage forms set out above, the compositions of the present invention may also be administered by controlled release means and delivery devices. In particular their dosage unit form may consist of a coated tablet wherein the tablet coating comprises an effective amount of a compound (ii)—as described hereinabove—and the tablet core comprises an effective amount of a compound (i) and a swellable hydrophilic polymer, and wherein the tablet coating and the tablet core further comprise pharmaceutically acceptable carrier materials.

For the purpose of oral therapeutic administration, the compounds (i) and (ii) of the present invention may be incorporated into a solution or suspension. These preparations should contain at least 0.1% by weight of the active ingredients of the composition of the invention.

Such solutions or suspensions may also include one or more of the following adjuvants: a sterile diluent such as water for injection, physiologic saline solution, oils, polyethylene glycols, glycerine, propylene glycol or other synthetic solvents; antibacterial agents such as benzyl alcohol; antioxidants such as ascorbic acid or sodium bisulfite; chelating agents such as ethylene diaminetetraacetic acid; buffers such as acetates, citrates or phosphates and agents for adjusting of tonicity such as sodium chloride or dextrose. The preparation can be enclosed in ampules, or multiple dose vials made of glass or plastic.

The invention is further defined by reference to the following examples describing in detail the compositions of the present invention, as well as their utility.

While this invention has been described and illustrated with reference to certain preferred embodiments thereof, those skilled in the art will appreciate that various changes, modifications and substitutions can be made therein without departing from the spirit of the invention. For example, effective dosages other than the preferred ranges set forth hereinabove with respect to the active ingredients may be applicable as a consequence of variations of the responsiveness of the human treated, severity of symptoms, dosage related adverse effects, if any observed and similar considerations. Accordingly, such expected variations or differences in the practice of the present invention and the results obtained are contemplated in accordance with the objects and practices of the present invention.

The efficacy and safety of a composition of the invention were evaluated for the treatment of rhinitis, especially perennial and seasonal rhinitis, by the following phase III multicenter, double-blind studies. The composition of the invention was compared to:

the racemate of 2-[2-[4-[(4-chlorophenyl)phenylmethyl]-1-piperazinyl]ethoxy]-acetic dihydrochloride, hereinafter referred to as "cetirizine" on the one hand, and (1S, 2S)2-methylamino-1-phenylpropan-1-ol hydrochloride, hereinafter referred to as "d-pseudoephedrine hydrochloride" or "pseudoephedrine" on the other hand.

For each study, patients enrolled were ranged in three therapeutic groups and were treated as follows:

Cetirizine group: a capsule containing 5 mg cetirizine and pseudoephedrine retard placebo to be taken morning and evening at meal times.

Pseudoephedrine group: a capsule containing 120 mg pseudoephedrine retard and cetirizine placebo to be taken morning and evening at meal times.

Composition group: a capsule containing 5 mg cetirizine and 120 mg pseudoephedrine retard to be taken morning and evening at meal times.

The patients' clinical evaluations made by the investigators at the end of the studies were based on a 5-point scale (0= worsening; 1=no change; 2= slight improvement; 3=good improvement; 4=more symptoms). The Cochran-Mantel-Haenszel test was used to compare the frequency distribution of the three groups, and for specific comparisons.

For each study, the global evaluation was completed with the following data:

At home, patients had to fill a daily record card where the five following symptoms were evaluated: sneezing, runny nose, blocked nose, itchy nose and itchy eyes. The symptoms scores were based on a 4-point scale (0: absent; 1: mild; 2: moderate; 3: severe). Cumulative relative frequencies PDS0 (percentage of days with a maximal score equal to 0) and PDS1 (percentage of days with a maximal score inferior or equal to 1) were calculated from the maximal score, ie the greater recorded score, irrespective of the symptom. Global comparisons were made using the Kruskal-Wallis test and specific comparisons were made with the Wilcoxon rank sum test.

Three visits were planned during the study: enrolment visit (Visit 1), control visit (Visit 2) one week after visit 1 and final visit (Visit 3). At visits 1 and 2, investigators evaluated the specific symptoms of allergic rhinitis (sneezing, rhinorrhea, nasal obstruction, nasal pruritus and ocular pruritus) using the 4-point scale (0: absent; 1: mild; 2: moderate; 3: severe). The rhinitis severity was evaluated by taking into account the maximal score of the five symptoms. The three groups were compared using the Cochran-Mantel-Haenszel test based on ranks.

The patients were asked about possible adverse events at each control visit. In each treatment group, adverse events were counted and grouped in classes. The frequency distributions of these adverse effect numbers were compared using the Cochran-Mantel-Haenszel test.

EXAMPLE 1

Evaluation in Perennial Allergic Rhinitis

A total of 554 patients were enrolled in this 3-week study. These patients ranged in age from 12 to 67 years old. They had to suffer from perennial allergic rhinitis diagnosed at least one year prior to the study, with radio allergosorbent test (RAST) or prick-test positive to perennial allergens including dust, mites and/or animal danders. On enrolment day, patients had to have the following symptoms: nasal obstruction, sneezing and rhinorrhea. The severity of rhinitis had to correspond to a score superior or equal to 2 for nasal obstruction, and to 5 for the sum of the three selected symptoms (scores were based on a 4-point scale (0: absent; 1: mild; 2: moderate; 3: severe). The characteristics of perennial allergic rhinitis were comparable in the three groups.

The global evaluation made by the investigators at the end of treatment (visit 3) showed that the patients categories "Good improvement" and "No more symptoms", when grouped, correspond to:

46% of the patients in the cetirizine group,

48% of the patients in the pseudoephedrine group,

53% of the patients in the composition group.

This global evaluation of the treatment showed the advantage of the composition of the invention compared to cetirizine or pseudoephedrine alone, that is confirmed by other results.

For example, the evaluation by patients at home has shown that the composition involved a better decrease of the symptoms than the two products taken on their own. The percentage of days PDS0 and PDS1 were higher with the composition compared to cetirizine alone or pseudoephedrine alone (Table 1). From a statistical point of view, the global comparisons showed a significant difference among the three groups of PDS0 (p=0.035); the composition was also statistically more effective than either of the two products taken on their own. For PDS1, the composition was statistically more effective than pseudoephedrine (p=0.022)

TABLE 1

Means of cumulative relative frequencies based on maximal symptom scores.

| | PDS0 | PDS1 |
|---|---|---|
| Cetirizine | 6.60% | 43.26% |
| Pseudoephedrine | 6.97% | 41.57% |
| Composition | 9.45% | 49.54% |

Evaluations made by the investigators during the visits for each symptom underlined an advantage of the composition. The evaluation based on the mean of the maximal 5-symptom scores (Table 2) showed a better efficacy of the composition compared to cetirizine or pseudoephedrine alone.

TABLE 2

Means of maximal 5-symptom scores at visits 1 and 2.

| | Visit 1 | Visit 2 |
|---|---|---|
| Cetirizine | 2.66 | 1.82 |
| Pseudoephedrine | 2.72 | 1.81 |
| Composition | 2.62 | 1.62 |

This study showed also that the three treatments were well tolerated. There were no significant differences between the three therapeutic groups as the proportion of patients with 0, 1, 2, 3, or more adverse events. However, the adverse events expected with pseudoephedrine (namely insomnia) were more frequent in the two groups taking pseudoephedrine, and sedation more frequent in the cetirizine group.

In conclusion, patients having taken the composition of the invention experienced more days with no symptom or with at most slight symptoms than patient in the other two therapeutic groups. These results confirm that the composition of the invention produces therapeutic improvement in perennial allergic rhinitis.

EXAMPLE 2:

Evaluation in Pollen-associated (or Seasonal) Allergic Rhinitis

A total of 687 patients enrolled in this 2-week study, their ages ranging from 12 to 67 years. They had to be suffering from pollen-associated allergic rhinitis, with a prick-test or a RAST positive to pollen. Most patients had an allergy to grass pollens (84%); 40% were allergic to weed pollens and 65% to tree pollens. On enrolment day, the patients had to be experiencing nasal obstruction and at least two of the four following symptoms: sneezing, rhinorrhea, nasal pruritus, ocular pruritus. The severity of rhinitis on enrolment day had to correspond to a score superior or equal to 2 for nasal obstruction, and to 8 for the sum of the five selected symptoms (scores were based on a 4-point scale (0: absent; 1: mild; 2: moderate; 3: severe). The characteristics of seasonal allergic rhinitis were comparable in the three groups.

The global evaluation showed an improvement with the composition of the invention compared with cetirizine or pseudoephedrine alone. The patients categories "Good improvement" and "No more symptoms", when grouped, correspond to:

56% of the patients in the cetirizine group,

58% of the patients in the pseudoephedrine group,

69% of the patients in the composition group.

These results are statistically significant. The composition of the invention is more effective than the two compounds taken on their own.

These results were confirmed by the evaluation by patients at home that showed a large decrease of the symptoms with the composition than with compounds taken on their own. The percentage of days PDS0 and PDS1 based on the maximal score of the five symptoms were higher with the composition (Table 3), and global comparisons are significant. Comparisons of composition versus cetirizine or pseudoephedrine alone are also statistically significant for PDS. From a statistical point of view, the compositions of the invention being always the most effective. The effects of the two products seem to be added up when they are taken in combination.

TABLE 3

Means of cumulative frequencies based on maximal symptom scores at visits.

|  | PDS0 | PDS1 |
|---|---|---|
| Cetirizine | 6.41% | 39.81% |
| Pseudoephedrine | 5.44% | 37.21% |
| Composition | 10.49% | 50.45% |

The evaluations made by the investigators during the visits show the greatest effectiveness was achieved by the composition compared to the individual compounds taken on their own. Regarding the maximal scores of the five symptoms at visit 2 (Table 4), the composition is more effective than either of the two medications taken on their own; global comparison and comparisons of cetirizine or pseudoephedrine versus composition are statistically significant.

TABLE 4

Means of maximal 5-symptom scores at visits 1 and 2.

|  | Visit 1 | Visit 2 |
|---|---|---|
| Cetirizine | 2.77 | 1.76 |
| Pseudoephedrine | 2.78 | 1.82 |
| Composition | 2.79 | 1.53 |

The three treatments were well tolerated, with few adverse effects (Table 5). The proportions of patients with at least one adverse effects are 23% in the-cetirizine group, 30% in the pseudoephedrine groups and 30% in the composition group. No significant difference (p=0.186) was shown between the three groups regarding the proportion of patients with 0, 1, 2, 3 or more adverse effects. No serious adverse event was reported in this study.

TABLE 5

Incidence of main adverse events.

|  | Cetirizine | Pseudoephedrine | Composition |
|---|---|---|---|
| Asthenia | 4% | 1% | 2% |
| Headache | 4% | 7% | 4% |
| Somnolence | 6% | 3% | 1% |
| Insomnia | 0% | 8.5% | 6.5% |

These results demonstrate that the treatment for pollen-associated allergic rhinitis is improved significantly by using the composition of the invention. From the investigators' point of view, the composition led to complete relief or to good improvement of the symptoms with 69% of the patients.

What we claim is:

1. A pharmaceutical composition which comprises a therapeutically effective amount of a mixture consisting essentially of
   (i) pseudoephedrine, an individual optical isomer or a pharmaceutically acceptable salt thereof, and
   (ii) at least one compound selected from 2-[4-(diphenylmethyl)-1-piperazinyl]-acetic acid or amide derivatives, an individual optical isomer or a pharmaceutically acceptable salt thereof.

2. A composition according to claim 1, wherein the 2-[4-(diphenylmethyl)-1-piperazinyl]-acetic acid or amide derivative is a compound having the formula

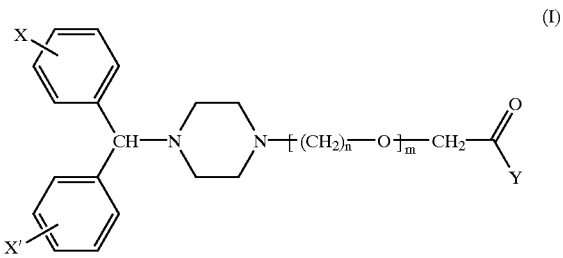

(I)

wherein

Y is a hydroxyl group or an —NH$_2$ group,

X and X' represent independently a hydrogen atom, a halogen atom, a straight or branched chain lower alkoxy radical or a trifluoromethyl radical, m is 1 or 2, and n is 1 or 2.

3. A composition according to claim 2, wherein X and X' are each independently selected from hydrogen, chlorine and fluorine atoms.

4. A composition according to claim 1, wherein the said compound (ii) is selected from:

2-[2-[4-[(4-chlorophenyl)phenylmethyl]-1-piperazinyl] ethoxy]-acetic acid or its dihydrochloride; potassium 2-[2-[4-[(4-chlorophenyl)phenylmethyl]-1-piperazinyl] ethoxy]-acetate;

2-[2-[4-(diphenylmethyl)-1-piperazinyl]ethoxy]-acetic acid or its dihydrochloride;

2-[2-[4-[(4-fluorophenyl)phenylmethyl]-1-piperazinyl] ethoxy]-acetic acid or its hydrate;

2-[2-[4-[bis(4-fluorophenyl)methyl]-1-piperazinyl]ethoxy]-acetic acid;

2-[2-[4-(diphenylmethyl)-1-piperazinyl]ethoxy]-acetamide or its dihydrochloride;

2-[2-[4-[(2-chlorophenyl)phenylmethyl]-1-piperazinyl] ethoxy]-acetamide or its dihydrochloride;

2-[2-[2-[4-[(4-methoxyphenyl)phenylmethyl]-1-piperazinyl]ethoxy]ethoxy]-acetamide or its dihydrochloride;

2-[2-[2-[4-(diphenylmethyl)-1-piperazinyl]ethoxy] ethoxy]-acetamide or its dihydrochloride;

2-[2-[2-[4-[(4-chlorophenyl)phenylmethyl]-1-piperazinyl] ethoxy]ethoxy]-acetamide or its dihydrochloride;

2-[2-[2-[4-(diphenylmethyl)-1-piperazinyl]ethoxy]ethoxy]-acetic acid or its dihydrochloride; and 2-[2-[2-[4-[(4-chlorophenyl)phenylmethyl]-1-piperazinyl] ethoxy]ethoxy]-acetic acid or its dihydrochloride.

5. A composition according to claim 1, wherein the said compound (ii) is selected from the racemate of 2-[2-[4[(4- chlorophenyl)phenylmethyl]-1-piperazinyl]ethoxy]-acetic acid, its levorotatory and dextrorotatory enantiomers and their pharmaceutically acceptable salts.

6. A composition according to claim 1 wherein the said mixture consists essentially of about 1 to about 30 percent by weight of the compound (ii) and of about 60 to about 99 percent by weight of the compound (i).

7. A composition according to claim 6 wherein the said composition consists essentially of about 3 to about 15 percent by weight of the compound (ii) and of about 85 to about 97 percent by weight of the compound (i).

8. A composition according to claim 1, also containing at least one pharmaceutically acceptable carrier or excipient.

9. A method of treating a disorder selected from rhinitis, cold, flu, cold-like and flu-like symptoms in a human, which comprises administering to a human in need of such therapy, simultaneously or not, an effective amount of pseudoephedrine, an individual optical isomer or a pharmaceutically acceptable salt thereof, and an effective amount of at least one compound selected from 2-[4-(diphenylmethyl)-1-piperazinyl]-acetic acid or amide derivatives, an individual optical isomer or a pharmaceutically acceptable salt thereof.

10. A method according to claim 9, wherein administration is effected simultaneously in the form of a pharmaceutical composition according to claim 1.

11. A method according to claim 10, wherein the said effective amount is from about 0.1 to about 6 milligram per kilogram of body weight per day.

12. A pharmaceutical composition according to claim 1, in the form of a dose containing about 15 mg to about 300 mg of the mixture of (i) and (ii).

13. A pharmaceutical composition according to claim 8, in the form of a coated tablet wherein the tablet coating comprises an effective amount of a compound (ii) and the tablet core comprises an effective amount of a compound (i) and a swellable hydrophilic polymer, and wherein the tablet coating and the tablet core further comprise pharmaceutically acceptable carrier materials.

14. A pharmaceutical composition according to claim 8, in the form of a capsule.

* * * * *